(12) United States Patent
Martin

(10) Patent No.: US 6,194,735 B1
(45) Date of Patent: Feb. 27, 2001

(54) GAS SENSOR

(76) Inventor: Hans Göran Evald Martin, Östansjö 2837 820 60, Delsbo (SE)

( * ) Notice: Subject to any disclaimer, the term of this patent is extended or adjusted under 35 U.S.C. 154(b) by 0 days.

(21) Appl. No.: 09/230,561

(22) PCT Filed: Aug. 20, 1997

(86) PCT No.: PCT/SE97/01366

§ 371 Date: Jan. 28, 1999

§ 102(e) Date: Jan. 28, 1999

(87) PCT Pub. No.: WO98/09152

PCT Pub. Date: Mar. 5, 1998

(30) Foreign Application Priority Data

Aug. 28, 1996 (SE) .................................................. 96 03109

(51) Int. Cl.⁷ .................................................. G01N 15/06
(52) U.S. Cl. ...................... 250/573; 250/222.2; 250/437; 250/632
(58) Field of Search ................................. 250/222.2, 573, 250/574, 576; 356/437, 438; 340/632; 73/23.2

(56) References Cited

U.S. PATENT DOCUMENTS

| | | | |
|---|---|---|---|
| 3,946,239 | 3/1976 | Salzman et al. | 250/461 B |
| 4,557,603 | * 12/1985 | Oehler et al. | 356/418 |
| 4,657,397 | 4/1987 | Oehler et al. | 356/414 |
| 5,009,493 | 4/1991 | Koch et al. | 350/619 |
| 5,170,064 | * 12/1992 | Howe | 250/573 |
| 5,767,967 | * 6/1998 | Yufa | 356/336 |
| 5,973,326 | * 10/1999 | Parrey et al. | 250/343 |
| 6,016,203 | * 1/2000 | Martin | 356/432 |

FOREIGN PATENT DOCUMENTS

WO97/18460  5/1997 (WO) .

* cited by examiner

Primary Examiner—Georgia Epps
Assistant Examiner—Tim Thompson
(74) Attorney, Agent, or Firm—Burns, Doane, Swecker & Mathis, LLP

(57) ABSTRACT

The invention relates to a gas sensor (A) which is adapted for evaluating the contents of a gas sample enclosed in a cavity (2) or a gas cell (1). The gas sensor has the form of a block in which the wall or wall-parts of a gas cell or cavity have highly light-reflective properties, designated mirror surfaces (11A, 12A). The cavity (2) has an opening (2a) for incoming light rays which are reflected in the cavity a predetermined number of times such as to create an optical analysis path before being caused to pass through an opening (6) for outgoing light rays, such reflections being achieved with the aid of three opposing, concave light-reflecting wall-parts (11, 12, 13). A first of the light-reflecting wall-parts (11) has the shape of part of an ellipsoid. A second (12) and a third (13) of the light-reflecting wall-parts have a common shape conforming to part of an ellipsoid. The focal points (11a, 11b) for the first light-reflecting wall-part (11) are disposed in or close to mirror surfaces (12A, 13A) for the second (12) and the third (13) wall-parts. A focal point (12a) for the second wall-part (12) and a focal point (13a) for the third wall-part (13) are located in or close to the mirror surface (11a) of the first wall-part (11).

26 Claims, 4 Drawing Sheets

GAS SENSOR

FIELD OF INVENTION

The present invention relates to a gas sensor and then particularly, but not exclusively, to a gas sensor with which the contents of a gas sample enclosed in a gas cell or cavity can be determined or analyzed, wherein the gas cell has the form of a block and the cavity walls or parts of said walls are highly reflective (mirror surfaces), wherein the cavity has an opening or some like means that functions to form incoming light rays into a light bundle, wherein the light bundle is intended to pass said cavity a predetermined number of times so as to define an optical analyzing path prior to the light rays being reflected by mutually opposite wall parts in a direction such as to pass through an opening or like means for outgoing light bundles, with the aid of at least three opposing, concave light-reflecting wall parts.

By the expression "openings or like means" is meant on the one hand that the cavity and mirror surfaces shall include at least one hole for receiving incoming light and at least one hole through which light exits, and that the light shall exit on one side of a mirror surface and shall enter on one side of a mirror surface on the other hand, in which application of the invention the mirror surfaces are whole. There is nothing to prevent light being allowed to enter on one side of a mirror surface and light to exit through one or more holes, or vice versa.

In addition to the aforesaid three opposing, concave light-reflecting wall parts, the cavity may also be delimited by further opposing light-reflecting wall parts. However, since the light reflected from these further wall parts will not contribute towards a better understanding of the present invention, the effect provided by said wall parts has not been described in this document.

A gas cell of this kind shall be coupled to a gas flow to be analyzed and to this end includes inlet and/or outlet openings, preferably in the form of tube or hose connections, although the principles of the invention can also be applied when the gas to be analyzed is allowed to diffuse into or out of the cavity.

A light source that has a frequency range adapted for determining the contents of the gas or gases under analysis, preferably an infrared light source, is connected to the gas cell and an opening, or like means, intended for the through passage of exiting, reflected light rays and located in wall parts of the cell, is provided with a wavelength selective filter, a spectral analyzing arrangement or like arrangement for evaluating the frequency-dependence of the light intensity and therewith determine the contents of the gas in question and/or the concentration of said content.

DESCRIPTION OF THE BACKGROUND ART

With regard to the earlier standpoint of techniques in the present context, reference is made to the subject matter of International Patent Publication PCT/SE96/01448 (corresponding to Swedish Patent Application No. 95 04020-0).

Reference is also made to this publication with regard to the definition of terms used in the present document.

With regard to the properties associated with the present invention, the teachings of the European Patent Publication 0 647 845 are also relevant with regard to the present standpoint of techniques, since it illustrates and describes a gas sensor that includes a gas cell which has a circular, concave mirror surface positioned opposite a concentrically orientated, circular-convex mirror surface, with the light source facing slightly to one side of the mutually coinciding centres of the mirror surfaces.

A gap in the convex mirror surface causes a slightly radially and outwardly directed light bundle with divergent light rays to be reflected alternately in concave and convex mirror sections, whereafter light rays are permitted to exit through a gap provided in the outer concave mirror surface, subsequent to having undergone a predetermined number of reflections and therewith having travelled through a predetermined optical light analyzing path of predetermined distance.

FIG. 6 of this prior publication illustrates an arrangement which is designed to enable the selection of one of two different optical analysis paths within the gas cell with the aid of separate light-ray exiting gaps and through a light-ray entering opening that is common to both analyzing paths.

It can be assumed that the described gas sensor is constructed so that its light receiving means is constructed to sense light rays that are coordinated to form a light bundle reflected in a convex mirror section in the gas cell and therewith a divergent light bundle.

Also forming part of the earlier standpoint of techniques is the arrangement of three partially spherical and opposing concave mirror surfaces designated "White" mirrors.

These mirrors are normally positioned at a relatively large distance from each other and the light source used is normally a laser light source.

A light bundle which contains more or less parallel light rays is reflected several times between the three opposing, spherically concave mirror surfaces, and when the last reflected light bundle is allowed to pass (adjacent the mirror edge) beyond a mirror surface, the light rays in the light bundle are received in a spectral analysis arrangement and evaluated in a known manner.

Also forming part of the earlier standpoint of techniques is the teachings of the Patent Publication U.S. Pat. No. 5,009,493. This publication describes an arrangement for a beam path in a multiple-reflection cell for measuring the absorption of light in a measuring gas. In the measuring arrangement, an entrance aperture is imaged on an exit aperture via an entrance aperture mirror, a field mirror and an exit aperture mirror.

This arrangement is improved in that the astigmatism of the imaging error is considerably reduced. For this purpose, the form of the aperture mirrors is approximately defined by an ellipsoid wherein the focal point spacing is approximately equal to half the distance between the entrance aperture and the exit aperture.

SUMMARY OF THE INVENTION

TECHNICAL PROBLEMS

When considering the fact that the technical deliberations which one of normal skill in this art must undertake in order to find a solution to one or more of the technical problems related to the analysis of gas and gas mixtures involve on the one hand the realization of those measures and/or sequence of measures that must be undertaken and on the other hand the selection of the means or those means required in to put these measures into effect make relevant the following technical problems in the development of the present invention.

When studying the known art referred to in the aforegoing, it will be seen that a technical problem resides in providing a gas cell that includes a gas inlet and/or a gas outlet or like means and that while using a light source which emits a light bundle into the cavity of the gas sensor or the gas cell causes the light rays to be reflected repeatedly between opposing concave wall parts that form either the whole of the cavity or a part thereof, and that is able to provide a predetermined number of reflections and therewith an optical analysis path of predetermined distance within the gas cell cavity, with the aid of a gas cell that has relatively small external dimensions and while applying the principles applicable to "White" mirrors but with the shape of the opposing mirror surfaces modified in accordance with the invention.

A technical problem resides in creating, with the aid of simple measures, conditions with regard to the mirror shapes of the concave wall-parts that will enable the light rays emitted by a light source to be converged and/or focused towards an outlet opening or like means even when the light bundle is initially pronouncedly divergent as it enters the cavity.

A further technical problem is one of realizing the advantages that are obtained when each of the three opposing mirror surfaces used has a domed shape with the dome smaller than half of a full ellipsoid and with the dividing plane of the dome located parallel with a chosen rotational axis of an ellipse.

It will be seen that a technical problem is one of realizing the advantages that are obtained when the dividing plane of the dome-shaped part is parallel with the major axis of the ellipse.

A further technical problem is one of realizing the conditions required to be able to use two almost identical ellipsoidal-parts and to position these parts with their concave mirror surfaces facing towards one another, such as to form the requisite cavity in the gas cell between said mirror surfaces.

A more qualified technical problem is one of realizing the advantages that are obtained when one of these ellipsoidal-parts is divided into two sub-parts and the conditions that are required in this respect, and thereafter either moving said parts towards one another or away from one another so as to form three opposing mirror surfaces with a reflected, wandering light bundle and focusing points within the cavity.

It will also be seen that a technical problem resides in creating, with the aid of simple means, conditions whereby with the aid of a single light source whose light beam is comprised of divergent light rays, and with the aid of two or more light exiting openings or like means in the gas cell, each with its respective spectral analyzing arrangement or the like, a gas sensor is able to determine the contents or a plurality of gases or gas mixtures and/or the concentrations of the gas constituents simultaneously in a gas cell and a cavity of one and the same construction.

It will also be seen that a technical problem resides in providing a gas sensor of relatively small external dimensions that is able to determine the concentration of a gas or a gas mixture within a wide analyzing range.

In this regard, a further technical problem is one of providing one and the same gas cell and one and the same cavity with conditions that will provide a desired wide analyzing range, by dividing the analyzing range so that it can be represented by optical analysis paths of mutually different lengths and thereby be able to readily use different optical analysis paths or distances within one and the same cavity in a gas cell.

It will also be seen that a technical problem is one of realizing the conditions that will enable two or more light-ray exiting openings or like means to be provided in the cavity or in the gas cell, and of realizing the significance of allowing each such opening to be positioned so as to represent a predetermined number of light-ray reflections and therewith a predetermined optical analysis path from the light source.

When a gas cell includes several light-ray exiting openings, a technical problem resides in realizing the significance of permitting one opening to represent an optical analysis path that deviates from the path afforded by each other opening, and the conditions required herefor.

Another technical problem is one of providing an inner structure with regard to opposing concave mirror surfaces which will enable the mirror surfaces to be readily coordinated and therewith provide a predetermined optical analysis path between light transmitter and opening gap or the like in a concave, large mirror section.

Another technical problem is one of providing an inner structure with regard to opposing concave mirror surfaces which will enable the mirror surfaces to be readily coordinated to provide two separate optical analysis paths from one and the same light transmitter with the same or different lengths between the light transmitter and opening gaps in associated mirror sections or the like.

Another technical problem is one of realizing the significance of including one or more openings or like means and to provide each of these openings or a number of said openings with a wavelength selective filter, such as an interference filter and/or a spectral analysis arrangement.

Another technical problem resides in providing a gas cell in which each of the concave, opposing light-reflecting wall-parts constitutes a portion, less than half, of an ellipsoid, and to give a first of said wall-part portions a length which enables it to be placed opposite to two coordinated portions of the second wall-part portion.

Another technical problem is one of realizing the significance of starting from two identical and mutually opposed ellipsoidal portions and that a shortening of the second portion, a predetermined section within the central region, and a bringing together of these, alternatively a division of the second portion and separation of said portions will provide a long optical analysis path corresponding thereto, with a possibility of a longer analyzing path with a smaller shortened section and/or a smaller separating displacement of said portions and vice versa.

Another technical problem resides in realizing the significance of and the advantages afforded by arranging the light source and/or the light-ray inlet opening centrally in a first wall-part or portion, while arranging the light-ray outlet openings or like means laterally within said first wall-part.

A technical problem also resides in realizing the significance of adapting the light source to a radiation angle that covers two mutually opposite second wall-part portions, so that each of said two second wall-part portions are able to reflect a respective one of two coordinated light-ray bundles, such that each of said bundles will be reflected between an opposing wall-part portion and a common wall-part portion.

Another technical problem also resides in the significance of arranging for a first light-ray bundle to exit through a first opening and a second light-ray bundle to exit through a second opening, said openings being positioned equally or unequally from the light source.

Another technical problem is one of realizing the significance of causing the diverging light rays transmitted from the light source to be reflected convergingly and thereafter reflected divergingly, convergingly, and so on, with the rays in the last reflection being convergent in a part of an ellipsoidal portion to produce an image of the light source at the light-ray exiting opening or openings or like means in the first light-reflecting wall-part.

It will also be seen that a technical problem is one of realizing the significance of and the advantages gained by the ability to move one or more light sources laterally from a central plane, such that each alternate reflection point in the first light-reflecting wall-part will be located on a respective side of said central plane, therewith enabling light-exiting openings or like means to be placed on the side of said central plane.

SOLUTION

With the intention of solving one or more of the aforesaid technical problems, the present invention takes as its starting point a gas sensor of the kind defined in the introduction, and proposes in particular that a cavity or a gas cell is configured such that a first light-reflecting wall-part has the form of part of an ellipsoid, and that second and third light-reflecting wall-part have a common configuration that also conforms to part of an ellipsoid.

According to preferred embodiments, the ellipsoidal portions have one and the same basic shape.

It is also proposed that the focal points of the first light-reflecting wall-part or the mirror surface are located in or close to the wall-parts or the mirror surfaces of the second and third wall-parts, and that a focal point for the second wall-part and a focal point for the third wall-part are located in or close to the wall-part or mirror surface of the first wall-part.

It is particularly proposed that the second and the third wall-parts are formed from part of an ellipsoidal portion and are obtained by dividing said ellipsoidal portion into two parts.

It is proposed in this respect that a divided section may be removed and the remaining sections displaced relative to one another in the direction of the rotational axis, or that a dividing section may mutually separate the remaining parts and that these parts are spaced at a given distance apart in the direction of the rotational axis.

According to the present invention, the cavity may include two or more openings or like means for outgoing light rays from a light source, and each opening is positioned so as to represent an optical analysis path of predetermined length.

According to preferred embodiments lying within the scope of the inventive concept, an opening shall be able to represent an optical analysis path from a light source that deviates from paths that are represented by other openings.

One or more openings will preferably be provided with a wave-length selective filter, such as an interference filter and/or a spectral analytical or spectral analyzing arrangement.

According to one preferred embodiment of the invention, mutually opposing light-reflecting wall-parts of the cavity shall consist of an identical or almost identical portion of an ellipsoid, wherein a first of said wall-parts is adapted to be placed opposite a two-part second wall-part.

The light source and/or the light-ray inlet opening may be disposed centrally in the first wall-part, and the light-ray outlet openings or like means may be side related in the first wall-part.

According to one embodiment of the invention, the light source may be adapted so that the radiation angle covers the two-part second and third wall-parts so as to cause two coordinated light bundles to be reflected a predetermined number of times between opposing wall-part sections, via said two wall-parts.

Light rays belonging to a first light bundle are arranged to exit through a first opening and light rays belonging to a second light bundle are arranged to exit through a second opening or like means.

According to one particularly preferred embodiment, light ray s that are-transmitted divergently from the light source are finally converged by the reflections to form an image of the light source at the light-ray exiting openings or like means.

According to another embodiment, the light source accommodating opening in the cavity is conveniently placed laterally of a central plane, wherewith each alternate reflection point in the first light-reflecting wall-part is located on a respective side of the central plane, therewith enabling light exiting openings to be placed on the side of said central plane.

ADVANTAGES

Those advantages primarily afforded by an inventive gas sensor are obtained by the provisions of conditions for creating in one and the same gas cell of small external dimensions provisions for a relatively long optical analysis path, by the arrangement of two opposing dome-shaped ellipsoidal concave mirror portions of which one is divided into two parts.

A gas cell of this kind is able to simultaneously determine the presence and/or the concentrations of the constituents of a plurality of different gases or gas mixtures by using two optical analysis paths of the same or different lengths within the gas cell, between a single light source and two or more outlet openings or like means, each provided with a respective wave length selective filter and/or spectral analytical arrangement.

Alternatively, the analyzing range and/or the analyzing sensitivity with respect to one and the same gas can be extended by choosing an optical analysis path of a first length for a first analyzing range and a second optical analysis path of a second length for a second analyzing range.

In addition, provisions are created for reflecting the light bundle transmitted from one of several light sources and containing diverging light rays in a manner to converge said light rays to form an image of the light source at the light ray exiting opening or openings or like means with regard to said light source.

The main characterizing features of a gas cell belonging to a gas sensor in accordance with the present invention are set forth in the characterizing clause of the following claim 1.

BRIEF DESCRIPTION OF THE DRAWINGS

An embodiment of a gas sensor and associated gas cell according to an embodiment at present described and having features significant of the present invention will now be described in more detail with reference to the accompanying drawings, in which.

DETAILED DESCRIPTION OF PROPOSED EMBODIMENTS

Figure 1:
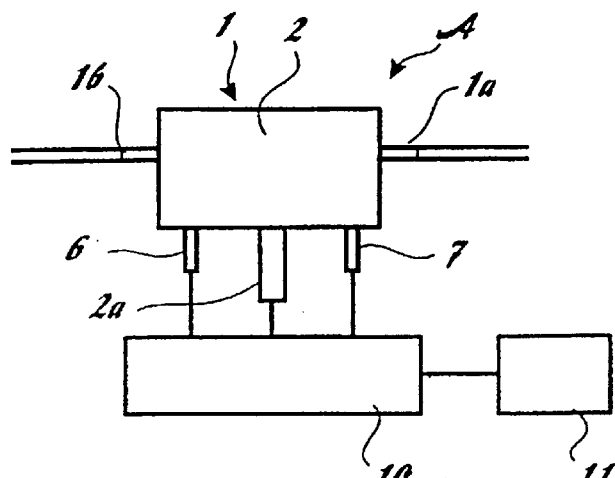
FIG. 1 is a greatly simplified illustration of a gas sensor having a gas cell in accordance with the invention and the electronics necessary for evaluating the frequency dependency of the light intensity within a spectral analytical or analyzing arrangement.

FIG. 1 is a greatly simplified illustration of a gas sensor "A" that includes a gas cell 1 and requisite electronics 10 for evaluating the frequency-dependency of the light intensity in a spectral analytical or analyzing arrangement 11.

The electronics 10 are designed to evaluate the frequency-dependency of the light intensity of a light bundle or light rays that pass through an outlet opening 6 and/or 7, and to compare the result of this evaluation with the frequency-dependency of the light intensity of a utilized light source 2a and, in response to an established discrepancy, analyze the gas or gas mixture enclosed in the cavity 2 of the gas cell 1 and also to determine the concentration of its constituents when required.

Because the principles of this kind of electronic equipment 10, 11 are known to the art, the equipment will not be described in more detail in this document.

Those modifications required to the equipment 10, 11 to evaluate the analysis results obtained with a gas cell in accordance with the present invention lie well within the normal expertise of the person skilled in this art.

A gas or a gas mixture is passed through a pipe connection 1a and into the cavity 2 of the gas cell 1, and exits through an outlet pipe connection 1b.

Figure 9:
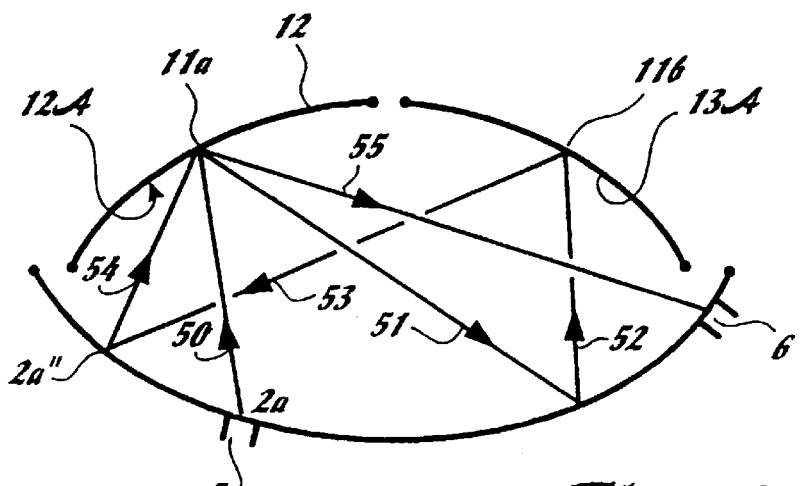
FIG. 9 illustrates a beam path (for the central beam) at a laterally positioned light source and illuminating initially a second mirror part, forming an optical analysis path that has five reflection points.
Figure 10:
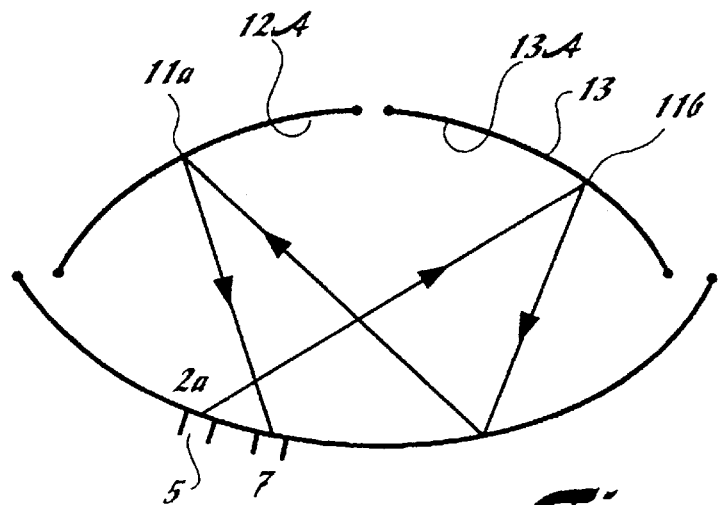
FIG. 10 illustrates a beam path (for the central beam) at a laterally positioned light source similar to that of FIG. 9 but illuminating initially a third mirror part that provides a shorter optical analysis path that includes three reflection points.

The gas cell 1 coacts with a light source 2a which directs a bundle of light rays into the cavity 2. The gas cell 1 also includes outlet openings 6, 7 for two mutually separate light ray bundles, preferably for mutually separate optical analysis paths (c.f. FIGS. 9 and 10).

The rays in the light bundle emitted from the light source 2a are highly divergent and shall be reflected a predetermined number of times between mutually opposing concave wall-parts that have been treated to form cavity delimiting mirror surfaces. Subsequent to being reflected a predetermined number of times and therewith having travelled through a predetermined optical analysis path, the light rays are able to pass convergently through an outlet opening (6 or 7).

That the optical analysis path is directly proportional to the number of reflections is an approximation that can be well accepted in this context.

The last reflection shall result in a convergent light bundle, so that the light source 2a can be imaged and the image focused in the proximity of the opposing mirror surface and in the opening (6 or 7) for more positive evaluation of the received frequency spectrum.

Figure 2:
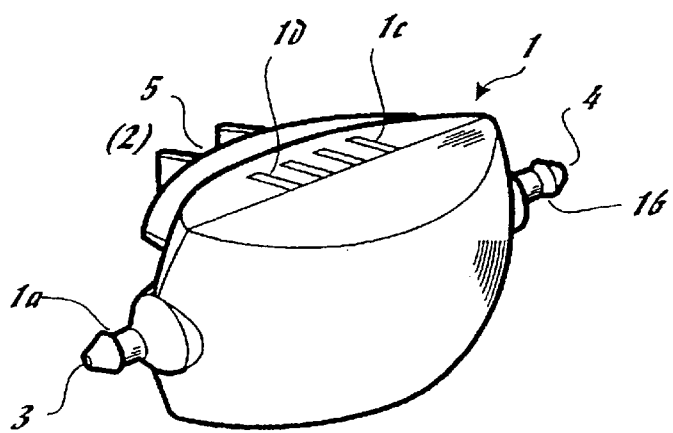
FIG. 2 is a first perspective view of the outer configuration of the gas cell.
Figure 3:
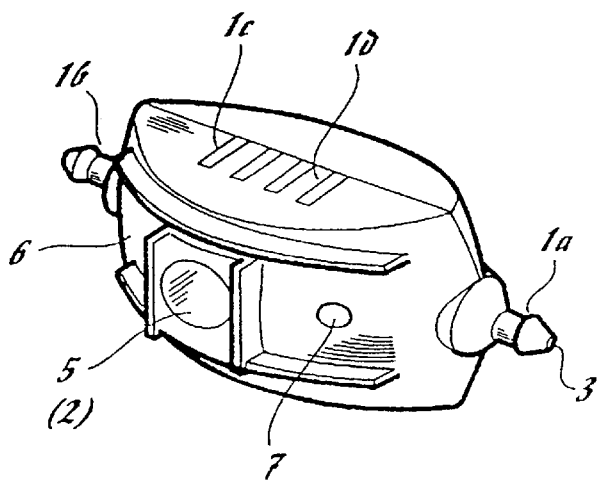
FIG. 3 is a second perspective view of the gas cell shown in FIG. 2.

FIGS. 2 and 3 are two different perspective views showing the external configuration of a gas cell that has features significant of the present invention with respect to the opposing light-reflecting wall-parts that have been treated to provide mirror surfaces, said gas cell also being referenced 1 in said Figures.

The gas sensor A is adapted to enable a gas sample enclosed in the cavity 2 of the gas cell 1 to be analyzed. The gas sample can be caused to pass through the cavity 2 via an inlet 3 (1a) and an outlet 4 (1b).

The gas cell 2 of this embodiment may also include one or more openings 1c, 1d through which the gas or gas mixture to be analyzed is able to pass by means of diffusion.

The illustrated gas cell 1 has the form of a block in which the wall or wall-parts of the cavity 2 have been treated in a known manner to provide the wall-parts with highly reflective properties with regard to the light rays, wherein the cavity 2 includes an opening 5 in the gas cell for accommodating a light source 2a which is driven by the electronics 10 so as to generate the requisite incoming light bundle.

The light source 2a mounted in the opening 5 may be adapted to transmit a light bundle in which the light rays have a frequency that lies in a relevant frequency range, such as in the infrared range. In the illustrated case, the light rays may diverge at an angle of about 120°.

For reasons of clarity, no light-generating unit 2a or light source 2a has been shown in FIGS. 2 or 3.

The light rays are now reflected a predetermined number of times between opposing mirror sections and thereafter exit through an opening 6 and/or through an opening 7. Each such opening has mounted therein a wavelength selective filter, a light sensitive means of known kind, although none of these has been shown in FIGS. 2 and 3 for the above said reason.

Also included in those light rays that exit through an opening are such light rays that are allowed to pass the edge of a mirror surface, which is typical with this technique although not illustrated here.

Figure 4:
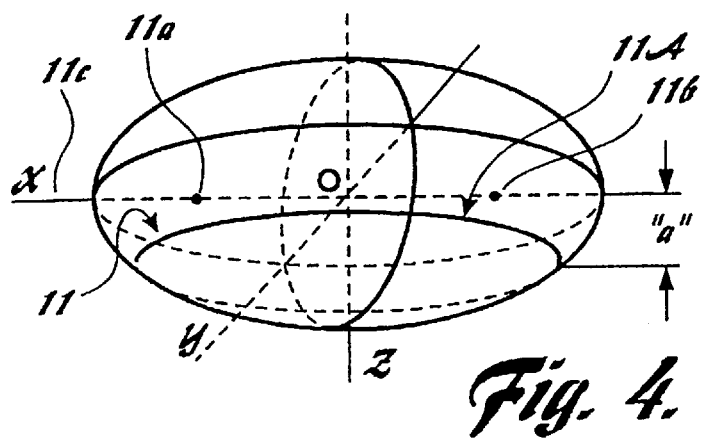
FIG. 4 is intended to illustrate the shape of a first concave wall-part or mirror surface of a chosen cavity.

FIG. 4 illustrates the chosen shape of a first light-reflecting concave wall-part 11 of the cavity.

Figure 5:
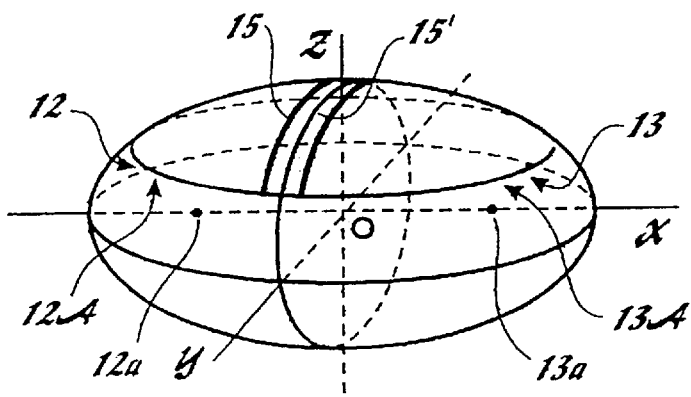
FIG. 5 is intended to illustrate the shapes of second and third concave wall-parts or mirror surfaces of the chosen cavity that oppose said first mirror surface.

FIG. 5 illustrates the chosen shape of second and third light-reflecting concave wall-parts 12 and 13 of the cavity.

The wall-parts 11, 12 and 13 have basically the same shape, i.e. the shape of an ellipsoid generated by rotating an ellipse about its major axis (x) (also referenced 11c).

A dome-shaped portion of the ellipsoid is formed by dissecting the ellipsoid in a plane parallel with the x-axis at a location at which said plane is located at a distance "a" from the major axis (x).

The concave surface in the ellipsoid portion 11 forms the mirror surface 11A with the focal points 11a and 11b located on the x-axis.

As shown in FIG. 5, the wall-parts 12 and 13 having the concave surfaces which form mirror surfaces 12A and 13A, with the focal points 12a and 13a located on the x-axis, are produced in a similar manner.

The wall-parts 12 and 13 in the cavity 2 are formed by removing a section 15 (in the z-/y-plane) and then bringing the wall-parts 12 and 13 together in the direction of the x-axis, wherewith the wall-parts 12 and 13 obtain in the x-axis a longitudinal extension which is slightly smaller than the longitudinal extension of the wall-part 11.

This embodiment will be described below in more detail.

In an alternative embodiment, a cut 15' is introduced in the plane "B" (z-/y-plane) such as to separate the wall-part portions 12 and 13.

This embodiment will not be described in detail, since it will be apparent from an understanding of the first-mentioned embodiment.

Figure 6:
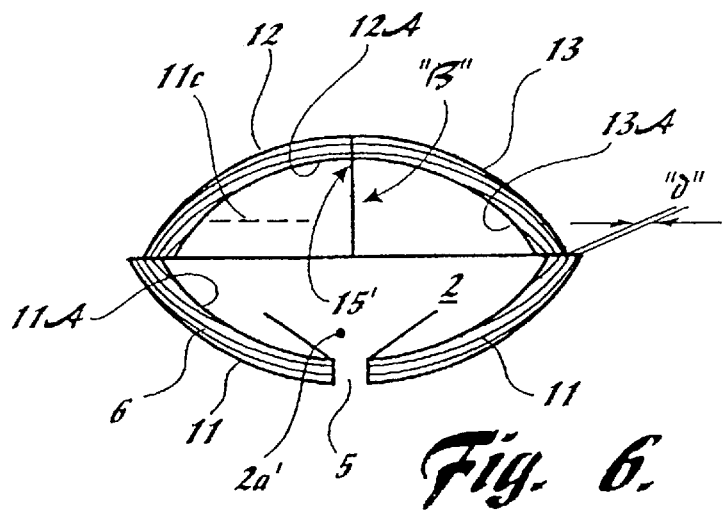
FIG. 6 is a view from above taken through a central plane (the x-z plane) geometry showing three opposing mirror surfaces included in a gas cell according to FIGS. 2 and 3.

FIG. 6 shows how the wall-parts 11; 12 and 13 are arranged to form the cavity 2. It will be evident from this Figure that incoming light rays 2a' arriving from the light source 2a and forming a divergent light bundle are first reflected convergently along a respective analyzing path by respective mirror surfaces 12a, 13a and thereafter reflected divergently by respective mirror surfaces 11A, and thereafter reflected convergently by the mirror surface 12A and 13A, and so on, so that the light bundle will travel through the cavity 2 a predetermined number of times and therewith form a well-defined optical analysis path prior to the light rays reflected by the wall-parts 12 and 13 being directed convergently through an opening 6 and through an opening 7 for outgoing light rays and through a filter, or some corresponding device, placed in respective openings (c.f. FIGS. 9 and 10).

In accordance with the invention, the light-reflecting function of the cavity 2 is achieved with the aid of three opposing concave light-reflecting wall parts 11, 12, 13 or mirror surfaces 11A, 12A and 13A, the nature and orientation of which will be described hereinafter in more detail with reference to FIGS. 7–10.

For the sake of simplicity, the following description has been limited to show one inlet opening 5 for incoming light bundle 2a' and one. or two outlet openings 6 and 7 for an outgoing convergent light bundle although it will be understood that more inlet openings can be used and one or more outlet openings for coaction with the same inlet opening.

Thus, it lies within the scope of the invention to create conditions that enable a plurality of inlet openings 5 to be provided, and to provide the cavity 2 with three, four or more outlet openings for convergent outgoing light bundles instead of only two such openings, wherein each opening may conveniently be positioned to represent a predetermined optical analysis path, i.e. a path corresponding to the reflection of light rays or a part of the light bundle a predetermined number of times between opposing concave mirror sections 11A, 12A and 13A.

Those measures and means required to take out the light rays at each focusing point occurring on the mirror surface 11A will be obvious to the person skilled in this art and the following description is therefore restricted solely to two outlet openings 6 and 7 for the sake of simplicity.

The invention is based on the concept of obtaining one or more relatively long optical analysis paths with a gas cell 1 of relatively small external dimensions.

Figure 8:
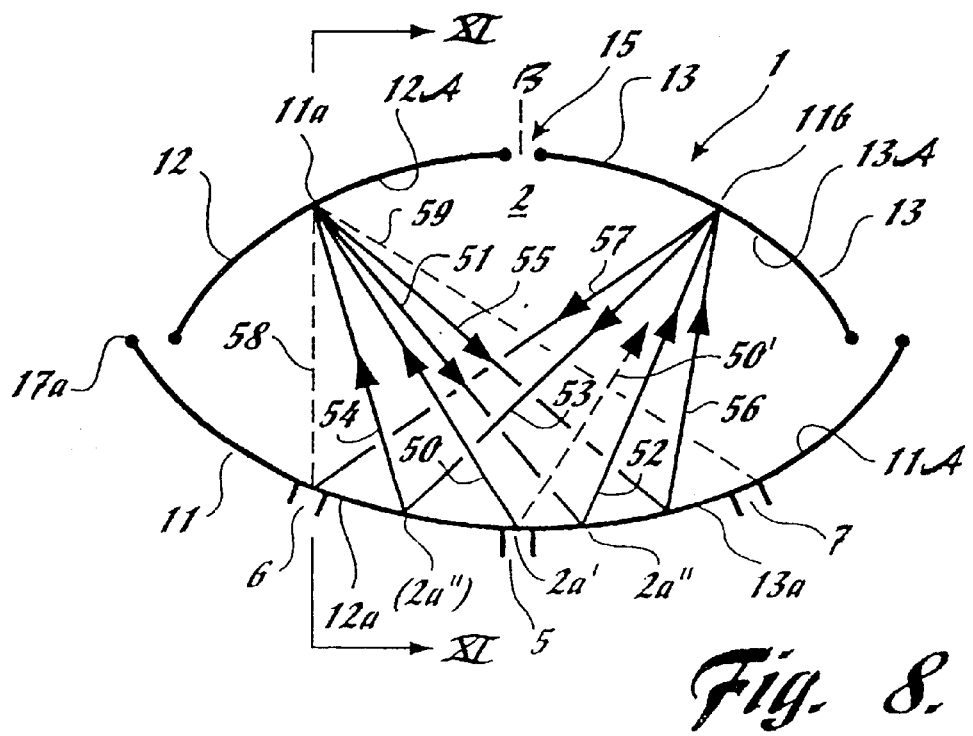
FIG. 8 illustrates in a central plane, by way of simplification, a first chosen beam path (for the central beam) representative of an optical analysis path from a light source to a first outlet opening, and shows a centrally placed light source that generates a divergent light bundle and enables (as shown in a broken beam path) two mutually separate optical analysis paths to be created within one and the same cavity and from one and the same light source.

The embodiment illustrated in FIG. 8 that includes a centrally located light source 2a (in the x-plane 13) and two outlet openings 6 and 7 placed equidistantly from the light source enables two identical optical analysis paths to be obtained with a "symmetric" orientation of the mirror surfaces 12A and 13A. Analyzing paths of mutually different lengths can be obtained, by changing the positions of the mirror surfaces 12 and 13 in relation to one another. Different optical analysis paths can also be obtained by changing solely the position of the light source 5 in the x-/z plane.

The constituents of two different gases or gas mixtures can be determined or measured by using two identical analyzing paths. The contents of two different gases or gas mixtures or, alternatively, two different analyzing ranges for one and the same gas can be determined by using two mutually different analyzing paths.

Preferably, one opening (6) will represent a position with an optical analysis path that deviates from each other opening (such as 7).

An interference filter or some corresponding device may be provided in one or more of said openings.

In accordance with the invention, the light source 2a provided in the proximity of the opening 5 and/or other openings for incoming light rays may be placed centrally in the first wall-part 11, as in the FIG. 8 embodiment, or placed on one side in accordance with the embodiments of FIGS. 9 and 10, or vice versa. This refers to orientation in the x-/z-plane, although it will be noted that the invention allows a degree of freedom also in the x-/y-plane, as shown more clearly in FIG. 11.

In accordance with the invention, the light source 2a may be placed in the gas cell in a recess 5 in the same mirror surface 11A as that in which the light exiting opening 6 and 7 are placed.

Figure 7:
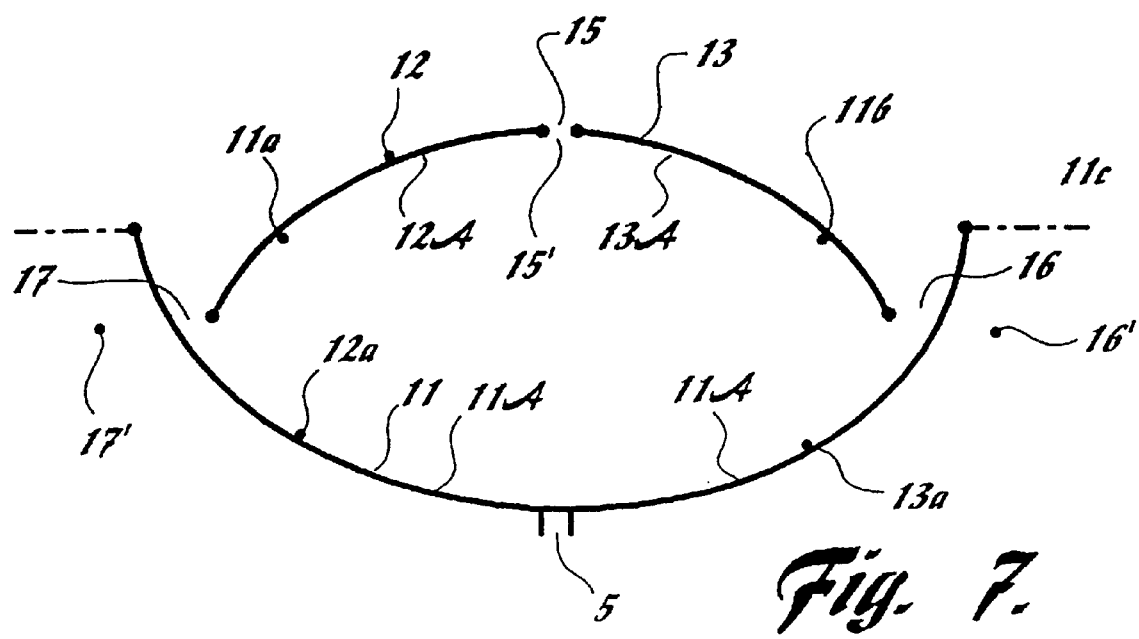
FIG. 7 is a sectional view similar to FIG. 6 with a central plane but with slightly enlarged opposing cavity-forming wall-parts which form mirror surfaces in the gas cell, and shows the orientation of associated ellipse centra.

Referring back to FIG. 6, and more particularly to FIGS. 7 and 8, it will be seen that the first wall-part 11 (in this plane) has a shape that conforms to a part of a complete rotational-elliptical shape with the focal points 11a and 11b located on an imaginary rotational line 11c (the x-axis).

The wall-part 11 can thus be considered to have a dome-shape whose dimensions are slightly smaller than one-half an ellipsoidal shape. A hole 5 for accommodating the light source 2a is placed centrally in the wall-part and a light exiting opening 6 is provided on one side of the hole 5. The mirror surface is referenced 11A.

The wall-part 11 is positioned opposite the wall-parts 12 and 13, and the wall-parts 12 and 13 are coordinated to exhibit essentially the same shape as the wall-part 11.

The wall-parts 12 and 13 are formed by dividing the wall-part into two portions 12, 13 in a plane "B"0 perpendicular to the rotational axis 11c.

A second wall-part 12 then obtains part of a rotational elliptical shape in the same way as the wall-part 11, but has been given a length along the rotational axis that is slightly smaller than a quarter of an ellipse and with its mirror surface 12A located in the focal point 11a.

A third wall-part 13 thus obtains an elliptical shape but has a length which is slightly smaller than a quarter of an ellipsoid and has its mirror surface 13A located in the focal point 11b.

The elliptical shapes of the wall-part 11 and the wall-parts 12 and 13 are therefore substantially identical, although with the difference explained in more detail above with reference to FIG. 5.

The focal point 12a and the focal point 13a are located in the mirror surface 11A.

The invention is based on the concept that in the case of identical, opposing partially ellipsoidal mirror surfaces, the light rays will be reflected only backwards and forwards, and that an "asymmetry" is required in order for reflection images, and particularly focused image points, to "wander". The smaller the asymmetry selected, the less the wandering tendency and therewith the greater the number of reflections and the longer the optical analysis paths.

Another variant is to divide the ellipsoidal portion (12, 13) in the plane "B" (the z-plane) and to move the thus formed parts 12 and 13 away from each other, so that the edges 16' and 17' will lie outside the wall-part 11.

The beam path for this variant has not been shown, however, although it will be apparent to one skilled in this technical field.

The light source 2a is adapted so that the angle defined by the light bundle 2a' will cover at least said two second wall-parts 12, 13 in FIG. 8.

FIG. 8 shows a light bundle path with the central ray 50 of the light bundle 2a' directed from the light source 2a onto the mirror surface 12A.

The light bundle (2a') is highly divergent in the illustrated case, and only the central ray 50 directed onto the mirror surface 12A is shown for reasons of clarity.

The light bundle, containing the light ray 50, is reflected convergently from the mirror surface 12A onto the mirror surface 11A and contains a light ray 51, said surface 11A having a focal point 2a" immediately to the right of the light source 2a. A first short optical analysis path can be created at the focal point 2a" when an opening is orientated at this point.

The light bundle is then reflected divergently, with a central light ray 52, onto the mirror surface 13A and from there is reflected convergently as a light ray 53 onto the mirror surface 11A that has a focal point (2a") to the left of the light source 2a.

In this way, this focusing point (2a") can be represented by a longer, a second, optical analysis path when an opening is orientated at this focal point.

It will be noted that the focal points (2a", (2a")) will be positioned further and further away from the light source 2a with each reflection and therewith become greater and greater by virtue of the mirror-arrangement.

The opening 6 may be placed immediately to the right of the light source 2a at a very short analyzing path to the focal point 2a", or slightly to the left of the light source 2a at a somewhat longer analyzing path at the focal point (2a").

The embodiment in FIG. 8 illustrates, however, a still longer optical analysis path, insomuch that the light ray 53 is reflected onto the mirror surface 12A as a light ray 54 and is reflected therefrom onto the mirror surface 11A in the form of a light ray 55, and could there be represented by an adapted optical analysis path.

However, the embodiment has been chosen to illustrate that the light ray 55 shall be reflected further onto the mirror surface 13A as a divergent light bundle (central ray 56) and reflected by said mirror surface 13A to the opening 6 as a convergent light bundle (central ray 57).

It will be found in this regard that a focused image to a 2a" (2a") of the light source 2a will wander further and further from the central position of the light source 2a in the mirror surface 11A, and that the opening 6 could be placed still further up towards the edge 17a so as to obtain a longer optical analysis path.

The openings (6, 7) shall be positioned in the focal points formed, and a change in the orientation of the mirror surfaces 12A and 13A will result in changed positions of the formed focal points and therewith in changed positions of the openings.

It will be evident from this that if the mirror arrangement 11, 12 and 13 is changed slightly, the positions of the focal points will also change but will always be located on the mirror surface 11A.

It will be evident from the embodiment illustrated in FIG. 8 that it lies within the scope of the invention to place an opening 6 on the right side or the left side of the light source 2a. This means that in relation to the illustrated opening 6 an opening can be placed on the left side of the light source 2a (which is shown in FIG. 8 to be positioned centrally) slightly to the right of the illustrated position, wherewith the optical analysis path (50–53) will be smaller than if the change involved moving the opening to the left (as shown) for an optical analysis path (50–57).

Thus, in this case, the focused image 2a" of the light source 2a wanders from one side of the light source 2a to the other side thereof and constantly outwards from the light source 2a.

In a first embodiment, all light focused convergently in the mirror surface 11A is able to pass through the opening 6 for evaluation. However, it also lies within the scope of the invention to permit only a given frequency range to pass through the opening 6 by mounting an optical filter (not shown) in the opening, while enabling the remainder of the light to be reflected a further number of times (58, 59) and then taken out through another opening 7 where another frequency range is evaluated. This enables different gases to be analyzed with the aid of one single light source in one single gas cell.

FIG. 8 also shows that the beam path (the central rays) within the cavity 2 will form a stylized "eight" and that the images focused on the mirror surface 11A can be taken out at the location where the determined analyzing path and focusing point occur. The focused images of the light source 2a will be decreasing towards the centre (5) and increasing away from said centre.

As indicated in FIG. 8, if two identical optical analysis paths are desired, a light ray 50' may be allowed to be reflected in the mirror surface 13A, wherein the light ray will be reflected in the same way as that described above while using an opening adapted for the selected analyzing path.

Thus, two different optical analysis paths (50, 50') can be chosen within one and the same gas cell having a construction in accordance with FIG. 8, each providing the possibility of identical or different optical analysis paths. it may be desired to detect outgoing light rays closer to the centre (5), so as to obtain more precise analyzing values that are more independent on the possible movement and positioning of the light source.

FIGS. 9 and 10 illustrate alternative beam paths (central rays) from a side-positioned light source 2a, therewith providing different optical analysis paths between the light source 2a and a selected opening 6 in FIG. 9 and a selected opening 7 in FIG. 10.

It will be noticed in this respect that a further opening 7 may be placed at a different distance from the light source 2a than the opening 6, so as to enable one and the same gas or gas mixture to be evaluated, or analyzed, within two different analyzing regions, one analyzing-region for the optical analysis path between the light source 2a and the opening 6 (FIG. 9) and one analyzing region which has a shorter optical analysis path between the light source 2a and the opening 7 (FIG. 10).

In the case of the FIG. 9 embodiment, the image 2a" (lacking the opening 6) will wander outwards from the light source 2a to the left, whereas in the case of the FIG. 10 embodiment the image 2a" will wander to the right from the light source 2a. The image 2a" will again wander outwards, when the centre or the light source 2a has been passed.

Figure 11:
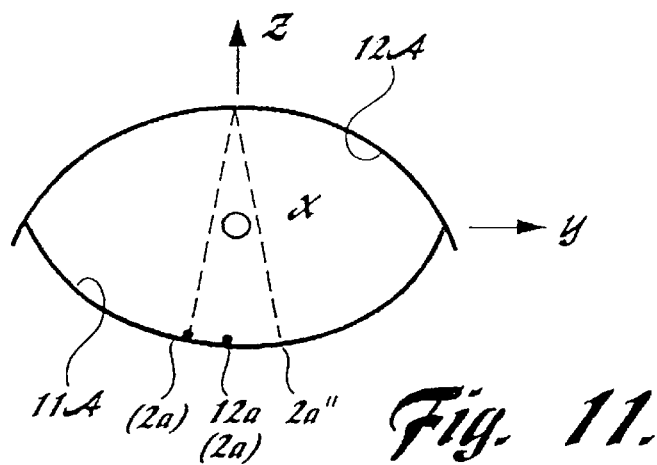
FIG. 11 is a sectional view of the cavity in the gas cell taken on the line XI—XI in FIG. 8.

FIG. 11 shows the cavity 2 in a y-/-z plane and in a sectional view taken on the line XI—XI in FIG. 8.

In the earlier described embodiments, the light source (2a) is positioned in the x-/z-plane. However, this Figure shows that if a light source is placed to the left of the plane (2a), the first focused image 2a" will be placed to the right of the central plane (the x-/z plane), the second image to the left of said central plane, and so on, therewith enabling the openings used to be mutually offset in relation to the central line.

It will be evident from this that one or more light sources may be used for one and the same cavity with one or more light-source associated openings.

It will be understood that the invention is not limited to the aforedescribed exemplifying embodiments thereof and that modifications can be made within the scope of the inventive concept as defined in the following claims.

What is claimed is:

1. A gas sensor for evaluating the contents of a gas sample enclosed in a cavity or a gas cell, wherein the gas sensor has the form of a block, wherein the wall or wall-parts of a gas cell or a cavity has/have high light-reflecting properties, designated mirror surfaces, wherein the cavity has an opening for incoming light rays that are reflected in said cavity a predetermined number of times so as to form an optical analysis path prior to the light rays reflected by said wall-parts being directed to exit through an opening for outgoing light rays with the aid of three opposing, ellipsoid concave light-reflecting wall-parts, wherein a first of said light-reflecting wall-parts has the shape of a part somewhat less than half of an ellipsoid; and wherein a second and a third of said light-reflecting wall-parts have a common part-ellipsoidal shape of somewhat less than half of an ellipsoid, said first wall-part and said second and third wall-parts are positioned adjacent one another, and the second and the third wall-parts are obtained by appropriate division of the ellipsoid.

2. A gas sensor according to claim 1, wherein the ellipsoidal parts have the same basic shape.

3. A gas sensor according to claim 1, wherein the focal points for the first light-reflecting wall-part are locate in or close to mirror surfaces on the second and third wall-parts.

4. A gas sensor according to claim 3, wherein a focal point for the second wall-part and a focal point for the third wall-part are located in or close to the mirror surface on the first wall-part.

5. A gas sensor according to claim 1, wherein said second and third wall-parts are formed from a part of an ellipsoid and that a section is removed from said ellipsoidal part and said wall-parts moved towards one another.

6. A gas sensor according to claim 1, wherein a dividing cut mutually separates the wall-parts, and in that said wall-parts are moved away from each other.

7. A gas sensor according to claim 1, wherein the cavity includes two or more openings for outgoing light rays; and in that each opening is positioned so as to represent a predetermined optical analysis path.

8. A gas sensor according to claim 7, further comprising an opening which is positioned to represent an optical analysis path that deviates from paths represented by other openings.

9. A gas sensor according to claim 7, wherein one or more openings are provided with wavelength selective filters, such as interference filters.

10. A gas sensor according to claim 1, wherein each concave light-reflecting wall-part is comprised of a dome-like part of an ellipsoid; and in that a first of said wall-parts is located opposite to two other wall-parts.

11. A gas sensor according to claim 7, wherein the light source and/or the opening for incoming light rays is located in said first wall-part.

12. A gas sensor according to claim 11, wherein the opening for outgoing light rays is provided in the first wall-part.

13. A gas sensor according to claim 7, wherein the light source is adapted to emit light at an angle that includes said two other wall-parts.

14. A gas sensor according to claim 13, wherein said two other wall-parts are operative in causing two coordinated light bundles to be reflected between opposing wall-parts.

15. A gas sensor according to claim 14, wherein light rays from a first light bundle are caused to exit through a first opening; and in that light rays from a second light bundle are caused to exit through a second opening.

16. A gas sensor according to claim 1, wherein the divergent light rays emitted by the light source are converged by said reflections to form an image of the light source at respective light ray exiting openings.

17. A gas sensor according to claim 1, wherein the first wall-part has a shape which conforms substantially to part of an ellipsoid, although somewhat less than half of an ellipsoid; and in that each of said second and third wall-parts have a shape which conforms essentially to, or somewhat less than, one-quarter of an ellipsoid.

18. A gas sensor according to claim 1, wherein the openings for outgoing light rays and/or incoming light rays are disposed on the side of a central plane.

19. A gas sensor according to claim 1, wherein two or more openings for incoming light rays are mutually side related.

20. A gas sensor according to claim 2, wherein the focal points for the first light-reflecting wall-part are located in or close to mirror surfaces on the second and third wall-parts.

21. A gas sensor according to claim 8, wherein one or more openings are provided with wavelength selective filters, such as interference filters.

22. A gas sensor according to claim 10, wherein the light source and/or the opening for incoming light rays is located in said first wall-part.

23. A gas sensor according to claim 11, wherein the light source is adapted to emit light at an angle that includes said two other wall-parts.

24. A gas sensor according to claim 7, wherein the divergent light rays emitted by the light source are converged by said reflections to form an image of the light source at respective light ray exiting openings.

25. A gas sensor according to claim 16, wherein the first wall-part has a shape which conforms substantially to part of an ellipsoid, although somewhat less than half of an ellipsoid; and in that each of said second and third wall-parts have a shape which conforms essentially to, or somewhat less than, one-quarter of an ellipsoid.

26. A gas sensor according to claim 18, wherein two or more openings for incoming light rays are mutually side related.

* * * * *